(12) United States Patent
Rothfuss et al.

(10) Patent No.: US 12,721,588 B2
(45) **Date of Patent: *Sep. 1, 2026**

(54) SYSTEM FOR AUTOMATIC AND EARLY DETECTION OF FREE FLAP FAILURE

(71) Applicant: UNIVERSITY OF PITTSBURGH—OF THE COMMONWEALTH SYSTEM OF HIGHER EDUCATION, Pittsburgh, PA (US)

(72) Inventors: Michael A. Rothfuss, Pittsburgh, PA (US); Ervin Sejdic, Pittsburgh, PA (US); Michael L. Gimbel, Pittsburgh, PA (US); Murat Akcakaya, Pittsburgh, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 359 days.

This patent is subject to a terminal disclaimer.

(21) Appl. No.: 18/484,624

(22) Filed: Oct. 11, 2023

(65) Prior Publication Data

US 2024/0041422 A1 Feb. 8, 2024

Related U.S. Application Data

(63) Continuation of application No. 16/630,964, filed as application No. PCT/US2018/042986 on Jul. 20, 2018, now Pat. No. 11,877,885.

(Continued)

(51) Int. Cl.
*A61B 8/06* (2006.01)
*A61B 5/00* (2006.01)

(52) U.S. Cl.
CPC .............. *A61B 8/06* (2013.01); *A61B 5/0004* (2013.01); *A61B 5/725* (2013.01); *A61B 5/7264* (2013.01); *A61B 2560/0219* (2013.01)

(58) Field of Classification Search
CPC ......... A61B 8/06; A61B 5/0004; A61B 5/725; A61B 5/7264; A61B 2560/0219; A61B 8/4227; A61B 8/4444; A61B 8/488
See application file for complete search history.

(56) References Cited

U.S. PATENT DOCUMENTS 4,752,843 A * 6/1988 Kim ........................ G11B 5/588 360/137
4,802,024 A * 1/1989 Knowlton ................ H04N 5/95 386/314

(Continued)

FOREIGN PATENT DOCUMENTS

WO 2017115104 A1 7/2017

OTHER PUBLICATIONS

Gestner, Brian, Jason Tanner, and David Anderson. "Glass break detector analog front-end using novel classifier circuit." 2007 IEEE International Symposium on Circuits and Systems (ISCAS). IEEE, 2007 (Year: 2007).*

*Primary Examiner* — Andrey Shostak
(74) *Attorney, Agent, or Firm* — Philip E. Levy; Eckert Seamans Cherin & Mellott, LLC

(57) ABSTRACT

A system for monitoring free flap patency includes transmit and receive transducers structured to be coupled to a blood vessel, and a plurality of circuitry modules structured to insonify a blood flow volume within the blood vessel and receive a scattered signal from the receive transducer, extract a baseband Doppler blood flow signal, $V_{BASEBAND}$, from the scattered signal, extract a plurality of features from $V_{BASEBAND}$, and classify the plurality of features and generate a binary signal based on the classification of the (Continued)

plurality of features, wherein the binary signal will have a first state responsive to the classification of the plurality of features indicating that a flow rate within the blood vessel is less than a predetermined level and a second state responsive to the classification of the plurality of features indicating the flow rate within the blood vessel is greater than or equal to the predetermined level.

5 Claims, 5 Drawing Sheets

Related U.S. Application Data

(60) Provisional application No. 62/539,043, filed on Jul. 31, 2017.

(56) References Cited

U.S. PATENT DOCUMENTS

| | | | | |
|---|---|---|---|---|
| 6,278,890 | B1 | 8/2001 | Chassaing et al. | |
| 2004/0082868 | A1 | 4/2004 | Campbell et al. | |
| 2004/0110221 | A1* | 6/2004 | Twine | G01N 33/57525 435/7.23 |
| 2005/0070799 | A1* | 3/2005 | Vilkomerson | A61B 5/6876 600/454 |
| 2010/0145210 | A1 | 6/2010 | Graff et al. | |
| 2012/0009612 | A1 | 1/2012 | Sitzman | |
| 2012/0101381 | A1 | 4/2012 | Palti | |
| 2013/0116575 | A1* | 5/2013 | Mickle | A61B 8/4227 600/479 |
| 2015/0063575 | A1 | 3/2015 | Tan | |
| 2016/0100790 | A1 | 4/2016 | Cantu et al. | |
| 2016/0135917 | A1 | 5/2016 | Mickle et al. | |
| 2016/0226508 | A1* | 8/2016 | Kurooka | H03M 1/485 |

* cited by examiner

70

$V_{DD}$
$M_1$
$M_2$
$M_3$
$V_{b1}$
$V_{b2}$
$V_{b3}$
$V_1$
$V_2$
$V_3$
$M_A$
$M_B$
$I_1$
$I_2$
$I_3$
$I_{thres}$
$I_m$
$I_{out}$
$I_{off}$
$V_{bthres}$
$V_{ref}$
$V_{out}$
$V_{boff}$
Vdd

SYSTEM FOR AUTOMATIC AND EARLY DETECTION OF FREE FLAP FAILURE

CROSS-REFERENCE TO RELATED APPLICATIONS

This application is a Continuation of U.S. patent application Ser. No. 16/630,964, filed on Jan. 14, 2020, entitled "SYSTEM FOR AUTOMATIC AND EARLY DETECTION OF FREE FLAP FAILURE", which is a U.S. National Stage under 35 USC 371 of PCT International Application No. PCT/US2018/042986, filed on Jul. 20, 2018, entitled "SYSTEM FOR AUTOMATIC AND EARLY DETECTION FREE FLAP FAILURE", which claims priority under 35 U.S.C. § 119(e) from U.S. Provisional Patent Application No. 62/539,043, filed on Jul. 31, 2017, entitled "SYSTEM FOR AUTOMATIC AND EARLY DETECTION OF FREE FLAP FAILURE", the contents of which are incorporated herein by reference.

BACKGROUND OF THE INVENTION

1. Field of the Invention

The present invention relates to free flap surgery, and, in particular, to a system for automatic detection of early onset of the failure of a free flap after free flap surgery.

2. Description of the Related Art

A flap is a piece of tissue that is used to cover a wound. A free flap is a piece of tissue that is disconnected from its original blood supply and is moved to a different part of the body and reconnected to a new blood supply.

Hourly blood vessel patency monitoring in the first few days after free flap surgery is crucial to the survival of the free flap transferred tissue. Loss of flow, if not caught promptly, can result in loss of the free flap, amputation, and death. Up to 10% of free flap cases are compromised in the post-operative monitoring period.

The current gold standard for free flap monitoring is the Cook-Swartz Doppler Probe and System. The Cook-Swartz Doppler Probe and System is comprised of a bedside monitor, a probe that affixes to the monitored blood vessel, and a wire tether to connect the probe to the bedside monitor. The wire tether can be easily snagged, resulting in misalignment of the probe on the vessel and even total disconnection of the wire from the probe.

False positive rates with the Cook-Swartz Doppler Probe and System can be as high as 30%. False positives result in costly surgical re-exploration (as much as $20,000-$30,000 per incident). Another problem with the Cook-Swartz. Doppler Probe and System is that it provides an audio output that requires human interpretation in order to make a judgment as to free flap patency (i.e., blood flow or no blood flow).

Typically, the venous outflow of a free flap is a better indicator of free flap patency as compared to monitoring arterial flow. Thus, it is often the venous outflow of a free flap that is monitored using the Cook-Swartz Doppler Probe and System. Unfortunately, it is very difficult to distinguish the venous flow audio signature from background noise due to the similarity of the two signals/sources. As a result, experienced personnel are needed to make a judgment as to free flap patency (i.e., blood flow or no blood flow) using the Cook-Swartz Doppler Probe and System.

M. A. Rothfuss, et al., "A system for simple real-time anastomotic failure detection and wireless blood flow monitoring in the lower limbs," *IEEE Journal of Translational Engineering in Health and Medicine*, vol. 4, pp. 1-15, 2016, describes a wireless implantable patency monitor for peripheral veins that was developed by a number of the present inventors. The described monitor provides a visual output from which clinicians are able to determine venous patency. However, from a clinical and usability perspective, the described monitor has a number of shortcomings. First, the baseline flow must be recorded to determine future flow status, and an experienced clinician is still needed to interpret the output. In addition, the monitor requires a high power budget because it digitizes blood flow waveform signals and transmits the data wirelessly to an external receiver for processing.

SUMMARY OF THE INVENTION

In one embodiment, an implantable system for monitoring patency of a free flap connected to a blood supply including a blood vessel in provided. The system includes a transmit transducer structured to be coupled to the blood vessel, a receive transducer structured to be coupled to the blood vessel, and a plurality of circuitry modules coupled to the transmit transducer and the receive transducer, wherein the plurality of circuitry modules are structured to: insonify a blood flow volume within the blood vessel through the transmit transducer and receive a scattered signal from the receive transducer, the scattered signal being generated in response to the blood flow volume being insonified, extract a baseband Doppler blood flow signal, $V_{BASEBAND}$, from the scattered signal, extract a plurality of features from $V_{BASEBAND}$, and classify the plurality of features and generate a binary signal based on the classification of the plurality of features, wherein the binary signal will have a first state responsive to the classification of the plurality of features indicating that a flow rate within the blood vessel is less than a predetermined level and a second state responsive to the classification of the plurality of features indicating the flow rate within the blood vessel is greater than or equal to the predetermined level.

In another embodiment, a method of monitoring patency of a free flap connected to a blood supply including a blood vessel is provided. The method includes insonifying a blood flow volume within the blood vessel, receiving a scattered signal, the scattered signal being generated in response to the blood flow volume being insonified, extracting a baseband Doppler blood flow signal, $V_{BASEBAND}$, from the scattered signal, extracting a plurality of features from $V_{BASEBAND}$, and classifying the plurality of features and generating a binary signal based on the classification of the plurality of features, wherein the binary signal will have a first state responsive to the classification of the plurality of features indicating that a flow rate within the blood vessel is less than a predetermined level and a second state responsive to the classification of the plurality of features indicating the flow rate within the blood vessel is greater than or equal to the predetermined level.

DETAILED DESCRIPTION OF EXEMPLARY EMBODIMENTS

Figure 1:
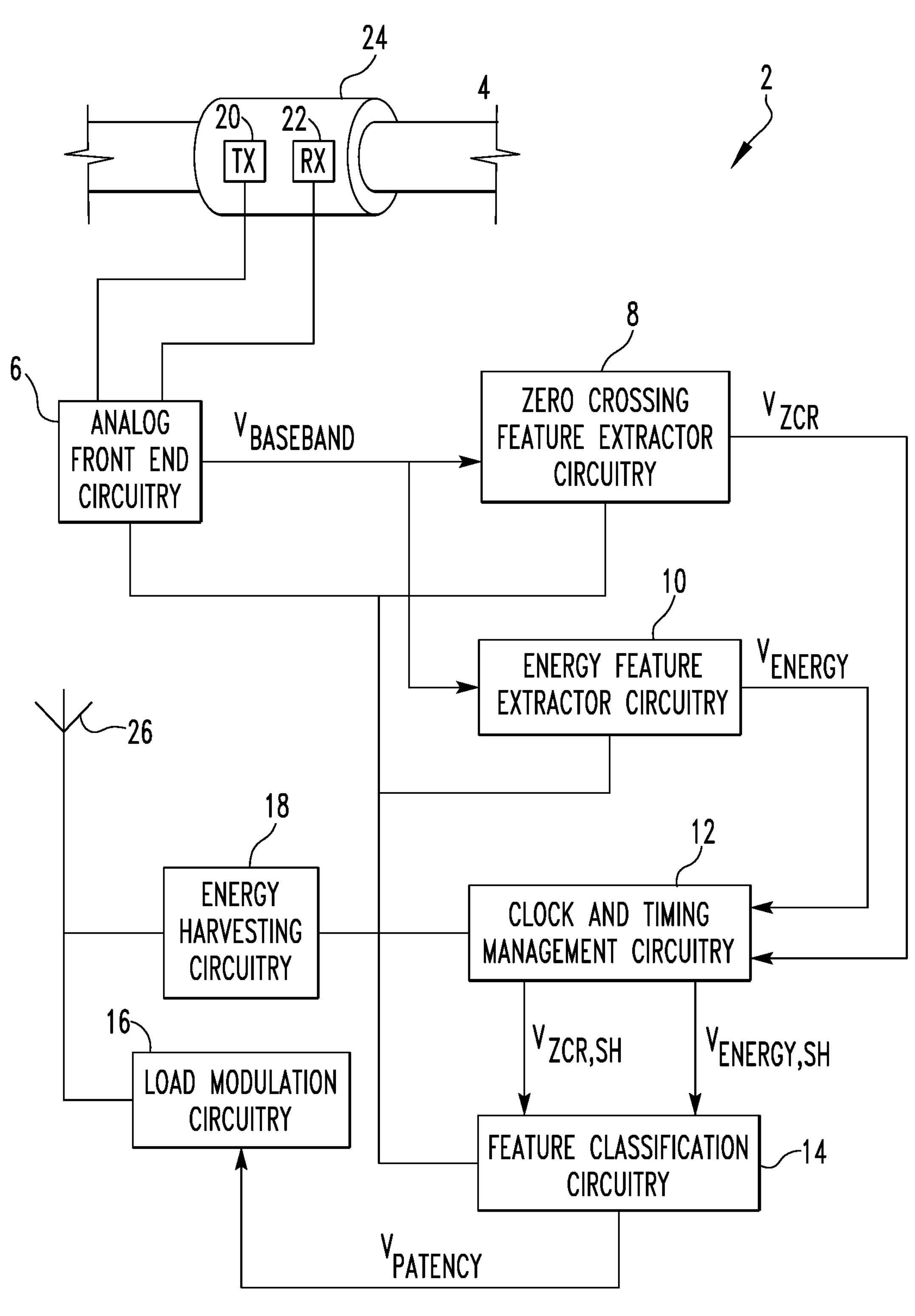
FIG. 1 is a schematic diagram of a free flap patency monitoring system according to an exemplary embodiment of the disclosed concept.

As used herein, the singular form of "a". "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As used herein, the term "number" shall mean one or an integer greater than one (i.e., a plurality).

As used herein, the term "hardware-only circuitry module" shall mean an electrical circuit module that does not include any hardware components that are capable of executing software programs/routines/algorithms, i.e., a circuit module that includes only hardware components that are not capable of executing software programs/routines/algorithms.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept will now be described, for purposes of explanation, in connection with numerous specific details in order to provide a thorough understanding of the subject innovation. It will be evident, however, that the disclosed concept can be practiced without these specific details without departing from the spirit and scope of this innovation.

As described in greater detail herein, the disclosed concept provides a system for automated free flap patency monitoring that eliminates the need for experienced personnel to participate in the decision-making process. The automated nature of the system and elimination of human interpretation will improve false positive rates. In addition, as discussed herein, the system of the disclosed concept employs feature extraction hardware/circuitry (in particular, zero-crossing and signal energy features) and classification/decision making hardware/circuitry (in particular, a two-dimensional dividing hyperplane) that makes the system particularly amenable to a microchip implementation wherein all of the blood flow information processing is performed in real time and on the implanted device, with the result being that only a simple "yes" or "no" status (i.e., a binary output) regarding free flap patency needs to be transmitted at the end of a measurement (e.g., at the end of a measurement window size/period as described herein). As a result, valuable radio frequency spectrum usage is significantly reduced as compared to devices that transmit digitized Doppler blood flow signals from the implanted device for subsequent analysis.

FIG. 1 is a schematic diagram of a free flap patency monitoring system 2 according to an exemplary embodiment of the disclosed concept. As described in detail herein, free flap patency monitoring system 2 is structured to determine the patency of a free flap connected to a blood supply including a blood vessel 4, which in the non-limiting exemplary embodiment is a vein, based upon the level of detected blood flow through blood vessel 4. In the exemplary embodiment, detected flow rates that are determined to be below a predetermined threshold flow rate level are deemed to be "no flow" and are considered a "positive" determination, meaning that the free flap is compromised (i.e., not viable), and detected flow rates that are determined to be greater than or equal to the predetermined threshold flow rate level are deemed to be "flow" and are considered a "negative" determination, meaning that the free flap is not compromised (i.e., viable). In the non-limiting exemplary embodiment, the predetermined threshold flow rate level is chosen to be 50% of a known baseline flow rate for the particular tissue in question, although it will be understood that other predetermined threshold flow rate levels may also be employed within the scope of the disclosed concept. Importantly, the predetermined threshold flow rate level may be chosen so as to establish a critical intervention point during the monitoring of a free flap.

As seen in FIG. 1, free flap patency monitoring system 2 includes several individual hardware circuitry modules (the majority of which are analog) that are structured to cooperate to monitor free flap patency based on detected flow rates. In particular, the hardware circuitry modules provided as part of free flap patency monitoring system 2 include analog front end circuitry 6, zero crossing feature extractor circuitry 8, energy feature extractor circuitry 10, clock and timing management circuitry 12, feature classification circuitry 14, load modulation circuitry 16, and energy harvesting circuitry 18. Each of these hardware circuitry modules is described in greater below.

In the non-limiting illustrated exemplary embodiment, free flap patency monitoring system 2 is a hardware-only implementation wherein the individual hardware circuitry modules are implemented as part of a monolithic microchip suitable for implantation in the body. In addition, in the non-limiting exemplary embodiment, and as described in more detail herein, free flap patency monitoring system 2 is implemented as a monolithic microchip that both receives power and communicates information wirelessly.

Referring to FIG. 1, analog front end circuitry 6 is coupled to a transmit piezoelectric transducer 20 and a receive piezoelectric transducer 22. Transmit piezoelectric transducer 20 and receive piezoelectric transducer 22 are inset to a cuff 24 that wraps around blood vessel 4. In addition, in the exemplary embodiment, transmit piezoelectric transducer 20 and receive piezoelectric transducer 22 are configured in a classic continuous wave (CW) Doppler configuration as described in, for example, U.S. Pat. No. 6,346,081. Analog front end circuitry 6 is structured to insonify the blood sample volume within blood vessel 4 using transmit piezoelectric transducer 20. Receive piezoelectric transducer 22 is structured to transduce the scattered signal that is generated as a result of the insonification of the blood sample volume within blood vessel 4. The transduced scattered signal is provided to analog front end circuitry 6, which in turn extracts the baseband Doppler blood flow signal, $V_{BASEBAND}$, from the scattered signal. As is known, $V_{BASEBAND}$ will have a frequency that is proportional to the velocity of the red blood cells (RBCs) in the blood sample volume within blood vessel 4 (RBCs are the primary scatterers/reflectors in blood because such a large portion of the blood volume is RBCs). In particular, it is known that the insonifying acoustic wave that is output by transmit piezoelectric transducer 20 and that impinges on the RBCs within the blood sample volume within blood vessel 4 will scatter isotropically with an intensity proportional to $f^4$ (i.e., Rayeligh scattering), so long as the wavelength of the wave is much larger than the RBCs and RBC aggregates. In addition, it is further known that the energy will be scattered at a frequency proportional to the velocity of the RBCs. The baseband Doppler signal may be extracted from the scattered signal in analog front end circuitry 6 using a zero-intermediate frequency (IF) mixer, where the resulting signal's frequency content represents the velocity of the RBCs. The Doppler frequency, fd, which is proportional to the velocity of the RBCs is defined by the well-known Doppler equation.

As seen in FIG. 1, analog front end circuitry 6 is coupled to both zero crossing feature extractor circuitry 8 and energy feature extractor circuitry 10, and the extracted $V_{BASEBAND}$ is provided to each of zero crossing feature extractor circuitry 8 and energy feature extractor circuitry 10. Zero crossing feature extractor circuitry 8 is structured to generate and output a continuous time signal, $V_{ZCR}$, which is a voltage signal that is a measure of the zero crossing rate of the raw baseband Doppler blood flow signal $V_{BASEBAND}$. $V_{ZCR}$ provides an estimate of the mean Doppler frequency of $V_{BASEBAND}$. Energy feature extractor circuitry 10 is structured to generate and output a continuous time signal, $V_{ENERGY}$, which is a voltage signal that is a measure of the energy of the raw baseband Doppler blood flow signal $V_{BASEBAND}$. In the exemplary embodiment, the maximum of $V_{BASEBAND}$ provides a reasonable estimate of signal energy during a predetermined window period.

Zero crossing feature extractor circuitry 8 and energy feature extractor circuitry 10 are both coupled to clock and timing management circuitry 12, and, as seen in FIG. 1, $V_{ZCR}$ and $V_{ENERGY}$ are provided as inputs to clock and timing management circuitry 12. Clock and timing management circuitry 12 is structured to provide clock synthesis, signal sampling and synchronization of system events for free flap patency monitoring system 2. With regard to signal sampling, clock and timing management circuitry 12 is structured to sample the $V_{ZCR}$ and $V_{ENERGY}$ (after a predefined period called the window size or window period) and generate a sampled $V_{ZCR}$ signal. $V_{ZCR,SH}$, and a sampled $V_{ENERGY}$ signal signal, $V_{ENERGY,SH}$, which are both discrete time voltage signals (i.e., $V_{ZCR,SH}$ and $V_{ENERGY,SH}$ are each a time series of a sequence of sampled data from the continuous signals $V_{ZCR}$ and $V_{ENERGY}$).

As seen in FIG. 1, $V_{ZCR,SH}$ and $V_{ENERGY,SH}$ are provided to feature classification circuitry 14. Feature classification circuitry 14 is, in the non-limiting exemplary embodiment, a monolithic decision circuit that implements a two-dimensional dividing hyperplane, where $V_{ZCR,SH}$ and $V_{ENERGY,SH}$ are classified as being on one side of the dividing hyperplane or the other. Feature classification circuitry 14 is structured to output a binary signal, $V_{PATENCY}$, which, in the exemplary embodiment, is high when "flow" is detected as described herein and low when "no flow" is detected as described herein. In other words, in the exemplary embodiment, a high $V_{PATENCY}$ signal indicates that the free flap is viable and not compromised (no surgery is needed) and a low $V_{PATENCY}$ signal indicates that the free flap is not viable and instead is compromised (surgery is needed).

As noted elsewhere herein, in the non-limiting exemplary embodiment, free flap patency monitoring system 2 is structured to be powered wirelessly and communicate information wirelessly. More specifically, with respect to wireless information communication, free flap patency monitoring system 2 is structured to be able to wirelessly transmit the $V_{PATENCY}$ signal outside of the body of the patient so that it can be used by an individual, such as a clinician, to assess the patency of the free flap in question. For this purpose, free flap patency monitoring system 2 includes load modulation circuitry 16 and energy harvesting circuitry 18, both of which are coupled to an antenna 26, such as, without limitation, a dipole antenna. Energy harvesting circuitry 20 is structured to receive RF energy from an external source, such as an RFID reader device, and harvest energy therefrom by converting (i.e., rectifying) the received RF energy into DC energy, e.g., a DC voltage. The DC energy is then used to power the circuitry of free flap patency monitoring system 2. Furthermore, in the exemplary embodiment, load modulation circuitry 16 is coupled to feature classification circuitry and receives the $V_{PATENCY}$ signal. Load modulation circuitry 16 is structured to modulate the RF carrier signal sent from the external source, such as an RFID reader device, in order to communicate the $V_{PATENCY}$ signal to the external source. In this exemplary implementation, the external source is thus able to "observe" the $V_{PATENCY}$ signal based on "load modulation." One particular manner in which such a wireless communication and power system may be implemented is described in detail in U.S. provisional patent application No. 62/336,897, entitled "Touch Probe Passively Powered Wireless Stent Antenna for Implanted Sensor Powering and Interrogation" and in PCT International Application No. PCT/US2017/031237, entitled "Touch Probe Passively Powered Wireless Stent Antenna for Implanted Sensor Powering and Interrogation" both of which are owned by the assignee of the disclosed concept. The disclosures of these applications are incorporated herein by reference.

It will be understood, however, that the just described wireless power and communication implementation is meant to be exemplary only and that other wireless power and communication implementations may also be employed within the scope of the disclosed concept. Moreover, it will be further understood that the disclosed concept is not limited to wirelessly powered implementations. Rather, the disclosed concept may also be implemented in connection with embodiments that employ on board storage such as an onboard battery (e.g., a rechargeable battery).

Figure 2:
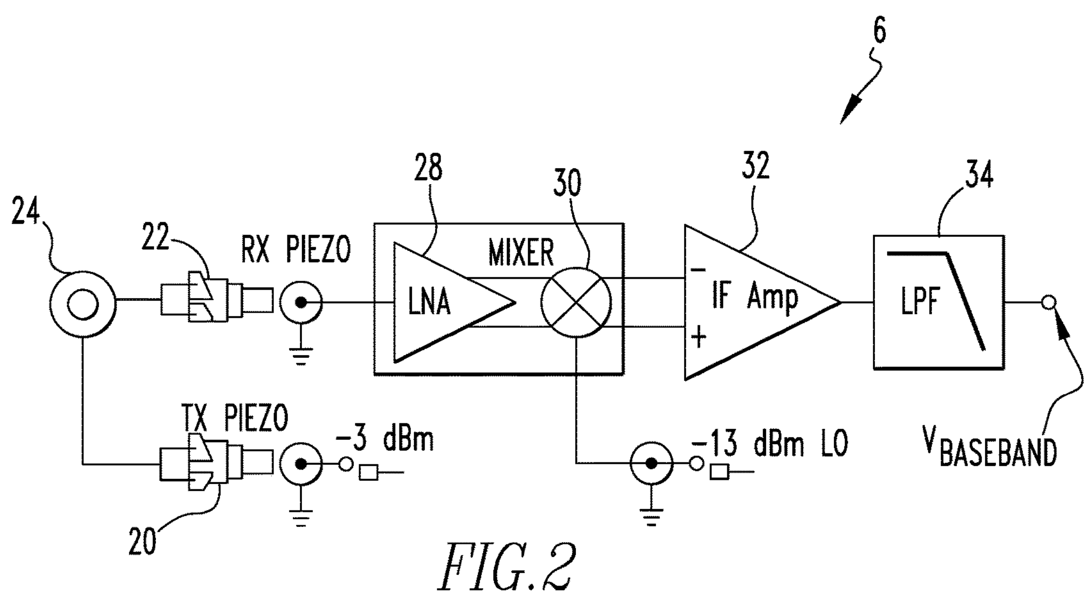
FIG. 2 is a schematic diagram of analog front end circuitry forming a part of the system of FIG. 1 according to one particular non-limiting exemplary embodiment of the disclosed concept.

FIG. 2 is a schematic diagram of analog front end circuitry 6 according to one particular non-limiting exemplary embodiment of the disclosed concept. In analog front end circuitry 6, transmit piezoelectric transducer 20 and receive piezoelectric transducer 22 are in a continuous wave (CW) configuration and are inset to cuff 24. Transmit piezoelectric transducer 20 is driven from a high-power high-frequency source (e.g., 500 microwatts) at the resonant frequency of transmit piezoelectric transducer 20 (e.g., 20 MHz). Transmit piezoelectric transducer 20 converts the electrical 20 MHz 500 microwatt signal into an ultrasonic acoustic wave that insonifies the blood flowing in blood vessel 4 (FIG. 1). The insonifying wave is scattered at a frequency deviation, from 20 MHz, proportional to the velocity of the red blood cells within the blood (i.e., the Doppler equation). The scattered acoustic wave is transduced by receive piezoelectric transducer 22 to a very low amplitude electrical signal. This low amplitude signal from receive piezoelectric transducer 22 drives the input of a low-noise amplifier (LNA) 28, which then drives a doubly balanced mixer 30, which then drives an intermediate frequency (IF) amplifier 32, which then drives a programmable low-pass filter 34. The output of low-pass filter 34 is $V_{BASEBAND}$, which, as described elsewhere herein, is the raw baseband Doppler blood flow signal. $V_{BASEBAND}$ is comprised of the spatial average of the frequency deviations (i.e., proportional to velocity) of the red blood cells within the insonifying volume. As described elsewhere herein, $V_{BASEBAND}$ drives both of the feature extraction modules, zero crossing feature extractor circuitry 8 and energy feature extractor circuitry 10. The $V_{BASEBAND}$ Signal resides, conveniently, in the audible range of human hearing (e.g., the $V_{BASEBAND}$ signal upper bandwidth limit may be about 8 kHz, with the human hearing upper bandwidth limit being about 20 kHz.).

Figure 3:
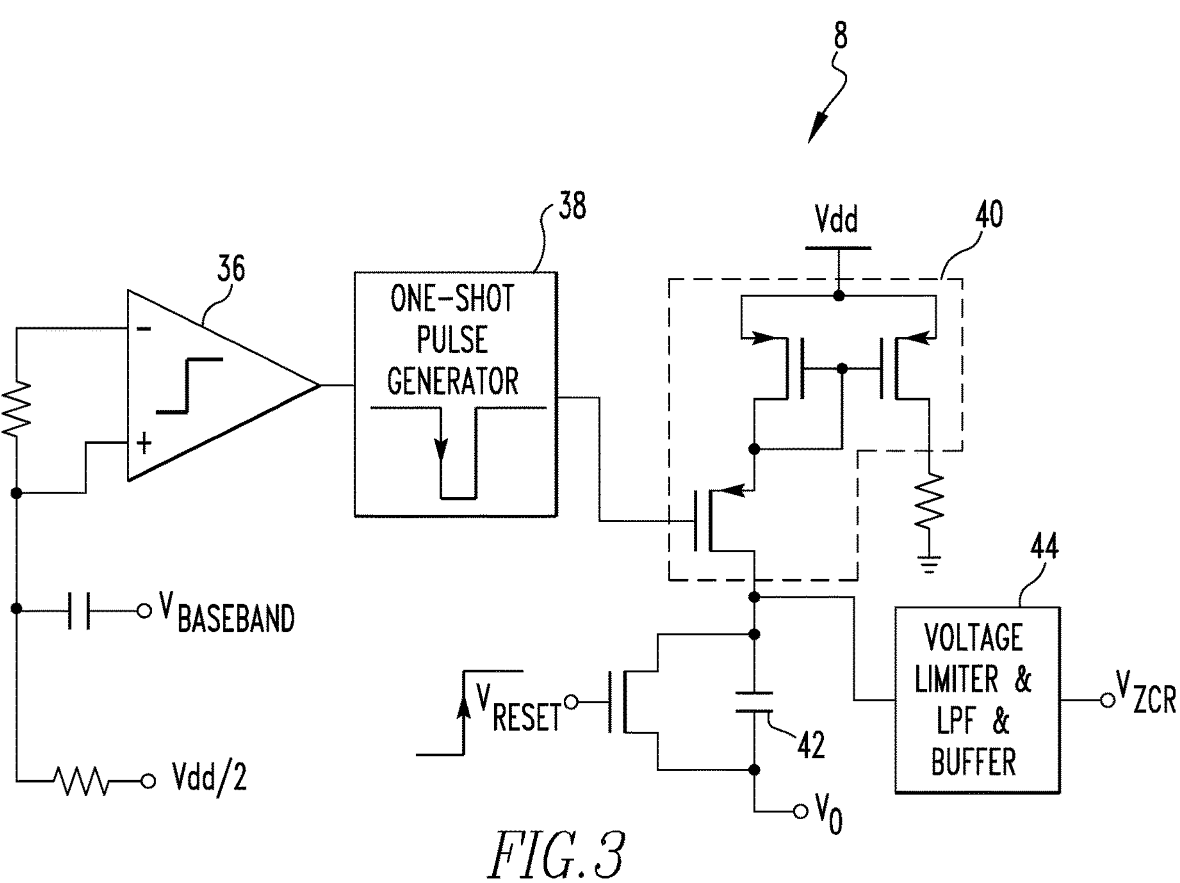
FIG. 3 is a schematic diagram of zero crossing feature extractor circuitry forming a part of the system of FIG. 1 according to one particular non-limiting exemplary embodiment of the disclosed concept.

FIG. 3 is a schematic diagram of zero crossing feature extractor circuitry 8 according to one particular non-limiting exemplary embodiment of the disclosed concept. Zero crossing feature extractor circuitry 8 is structured to detect negative-going (i.e., high-to-low) zero-crossings. To do this, first a comparator 36 toggles when any zero-crossing is detected. Comparator 36 drives a one-shot pulse generator 38, which is falling-edge triggered (i.e., sensitive only to negative-going zero-crossings). These one-shot pulses turn on a current source 40 (e.g., comprised of quad matched PMOS devices) that drives a current onto a sampling capacitor 42 for integration. The voltage on sampling capacitor 42 is processed by a voltage limiter and low-pass filter buffer 44 to confine the range of $V_{ZCR}$ between 0V-3.3V. The $V_{ZCR}$ voltage represents the $V_{BASEBAND}$ negative-going zero-crossings.

Figure 4:
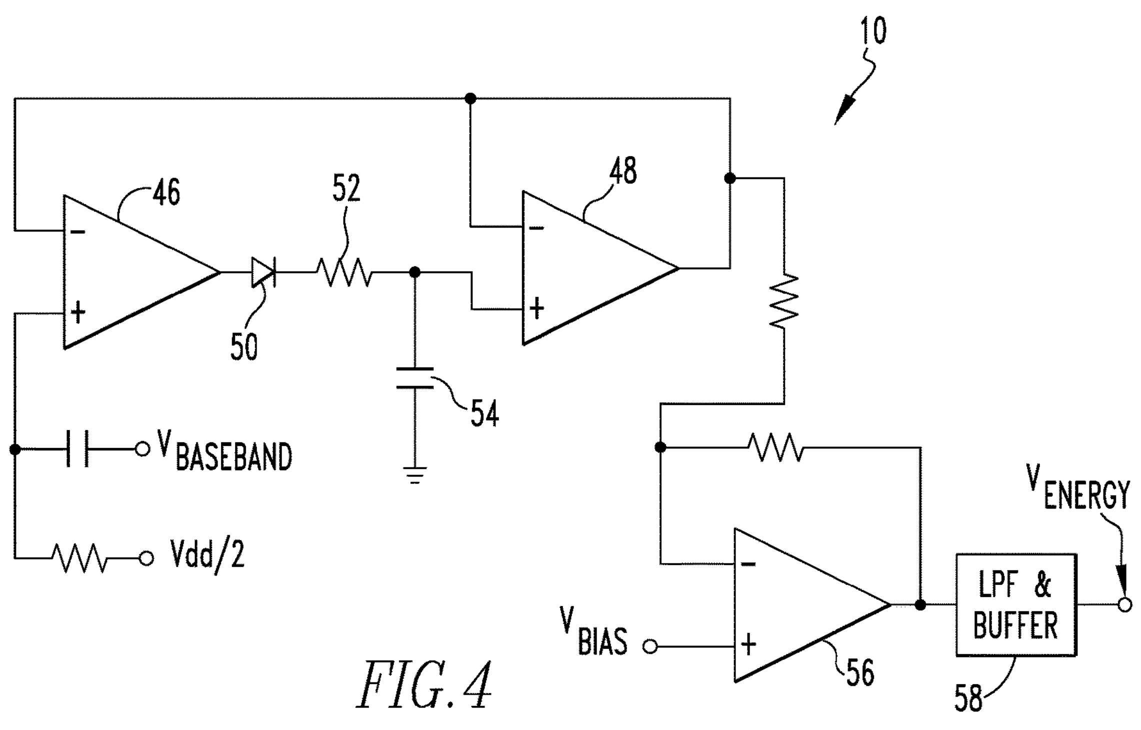
FIG. 4 is a schematic diagram of energy feature extractor circuitry forming a part of the system of FIG. 1 according to one particular non-limiting exemplary embodiment of the disclosed concept.

FIG. 4 is a schematic diagram of energy feature extractor circuitry 10 according to one particular non-limiting exemplary embodiment of the disclosed concept. Energy feature extractor circuitry 10 includes two op-amps 46 and 48, and a diode 50, a resistor 52, and a capacitor 54 located between the op-amps 46 and 48. These components form a peak detector that tracks the envelope of the $V_{BASEBAND}$ signal. Op amp 48 and an op amp 56 perform a signal inversion and level-shift so that the envelope signal range sits between 0V-3.3V. A low-pass filter and buffer 58 follows, and its output is $V_{ENERGY}$.

Figure 5:
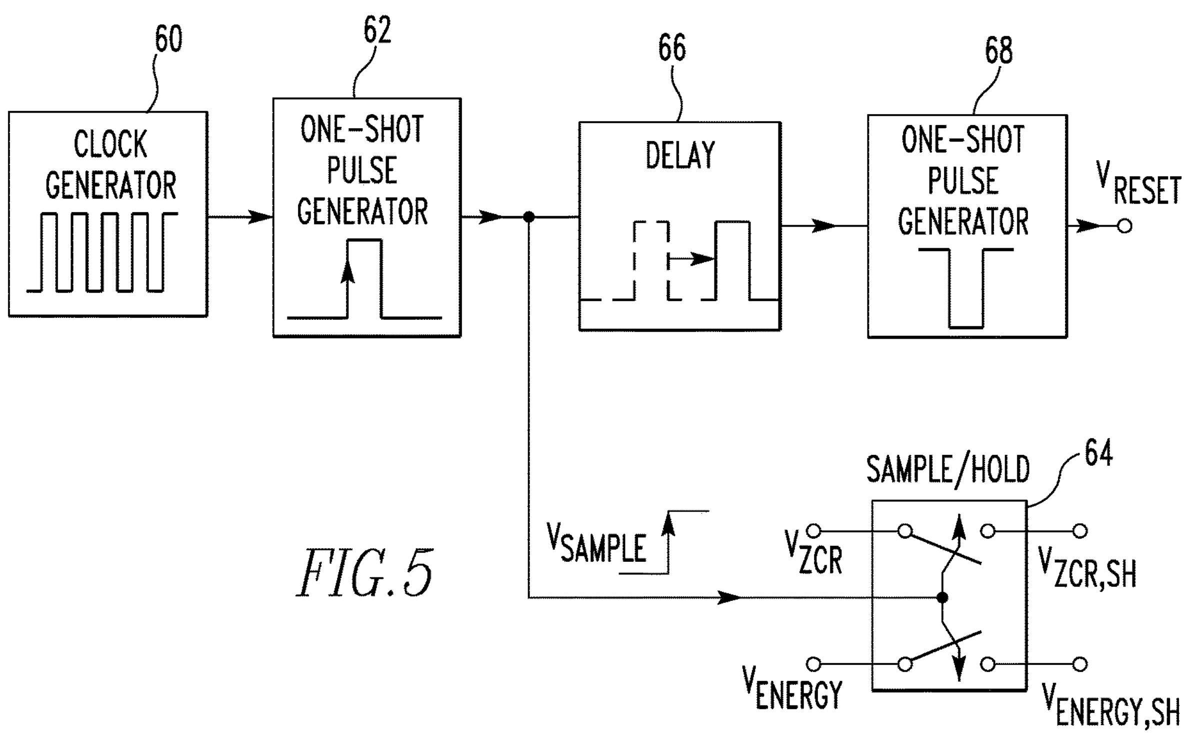
FIG. 5 is a schematic diagram of clock and timing management circuitry forming a part of the system of FIG. 1 according to one particular non-limiting exemplary embodiment of the disclosed concept.

FIG. 5 is a schematic diagram of clock and timing management circuitry 12 according to one particular non-limiting exemplary embodiment of the disclosed concept. As noted elsewhere herein, clock and timing management circuitry 12 performs timing functions and distributes clocks/pulses throughout free flap patency monitoring system 2. Clock and timing management circuitry 12 includes a clock generator 60 that generates a square-wave clock that drives a rising-edge one-shot pulse generator 62. Clock generator 60 sets the window period described herein (e.g., 50 ms). The output of one-shot pulse generator 62 is a pulse train of narrow-width pulses at a frequency equal to the frequency of clock generator 60. The output of one-shot pulse generator 62 also triggers sample/hold circuitry 64. Sample/hold circuitry 64 samples the continuous time $V_{ZCR}$ and $V_{ENERGY}$ Signals for the duration of the narrow-width pulse, and the sampled signal is held constant, as $V_{ZCR,SH}$ and $V_{ENERGY,SH}$, until another pulse triggers sample/hold circuitry 64, thus updating the $V_{ZCR,SH}$ and $V_{ENERGY,SH}$ voltages. Next, the output of one-shot pulse generator 62 drives an edge-triggered waveform-delay integrated circuit (IC) 66, followed by a falling-edge triggered one-shot pulse generator 68. One-shot pulse generator 62 and edge-triggered waveform-delay IC 66 form a dead-time generator (i.e., the two pulse-widths are non-overlapping and have a small dead-time between the two pulses). Thus, the output of the one-shot pulse generator 68 is a time-delayed version of the narrow-width pulse train of one-shot pulse generator 62. The output of one-shot pulse generator 68, $V_{reset}$, drives the NMOS device in zero crossing feature extractor circuitry 8 (FIG. 3), which shunts current away from storage capacitor 42 to reduce its stored charge, thus resetting the storage capacitor voltage to V0; V0 is near the ground voltage potential in the exemplary embodiment. The reason for doing all of this is evident by considering that the voltage on the sampling capacitor 42 must be sampled before it is reset. The reason for the reset in zero crossing feature extractor circuitry 8 and not energy feature extractor circuitry 10 is that zero crossing feature extractor circuitry 8 uses a storage element that integrates charge; whereas, the peak detector's output voltage in energy feature extractor circuitry 10 quickly decays to the instantaneous amplitude of $V_{BASEBAND}$. Putting this all together, in the exemplary embodiment, the window period is the observation period over which features of the $V_{BASEBAND}$ signal are computed; at the end of the observation period, the feature voltages $V_{ZCR}$ and $V_{ENERGY}$ are sampled and held constant; $V_{ZCR}$ and $V_{ENERGY}$ are updated at the end of each observation period.

In the non-limiting exemplary embodiment, when each of $V_{ZCR}$ and $V_{ENERGY}$ is sampled, the sample's amplitude voltage is held constant (i.e., only for the duration of the window period) and input into feature classification circuitry 14. The window size can be thought of as the observation time period (i.e., window) over which feature values are extracted. For example, if we have a 1.2 V 3 Hz signal (i.e., 1.2*cos[2*pi*3*t]) and a 3 second window size, then the zero-crossing feature will be equal to 18 (i.e., 2 zero-crossings per cycle, and 3 cycles per second, times 3 seconds), and the energy feature will be equal to 1.2 V. If the window were to be changed to 600 ms, the zero-crossing feature will be equal to 4, and the energy feature equal to 1.2 V. With regard to processing blood flow signal data, as window size is increased, the favorable results of improved sensitivity and specificity and false-positive rate are achieved. The present inventors have determined, however, that there is a diminishing return as window size is increased past approximately 50 ms.

Figure 6:
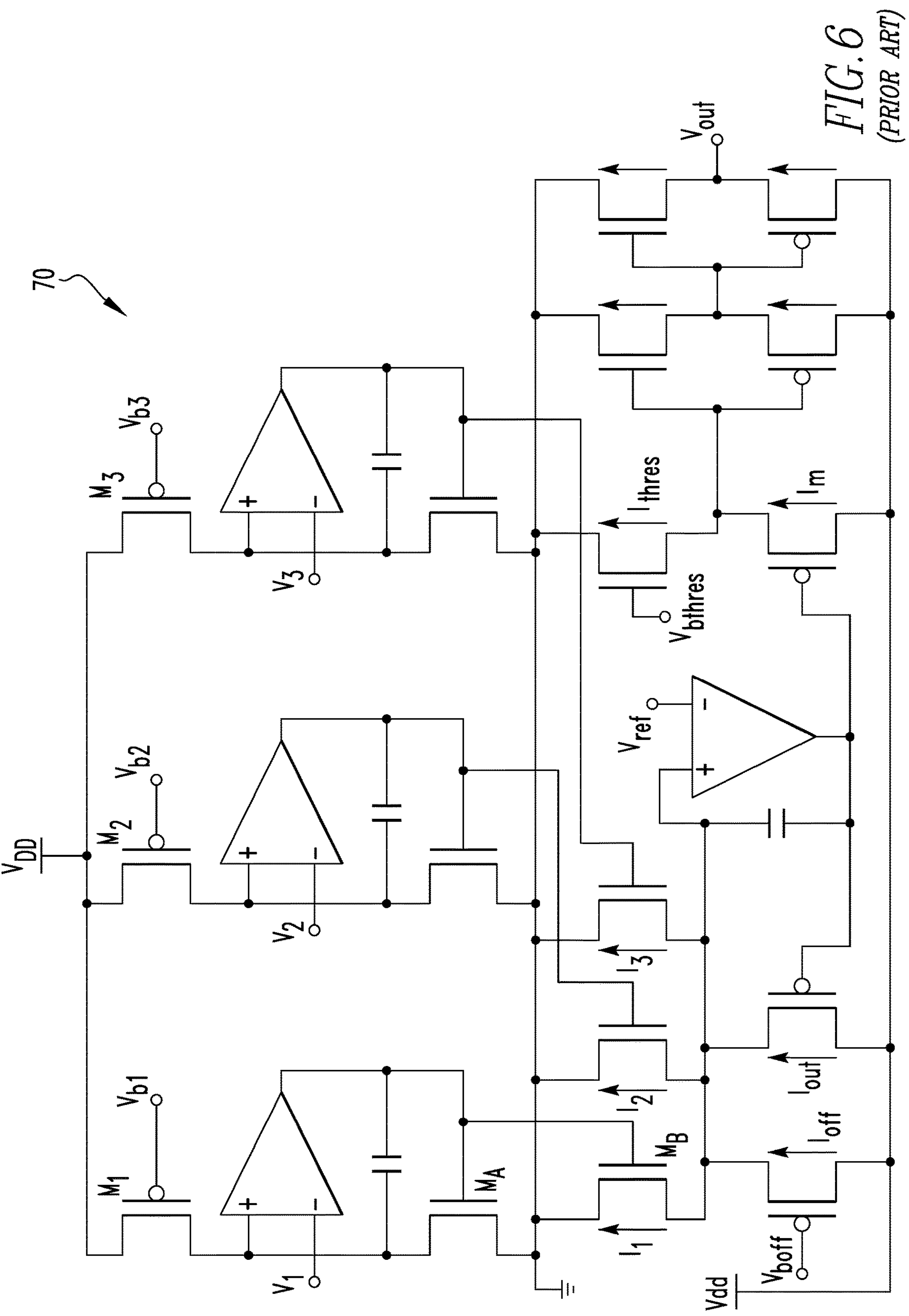
FIG. 6 is a schematic diagram of prior feature classification circuitry that may be used as a part of the system of FIG. 1 according to one particular non-limiting exemplary embodiment of the disclosed concept.

In the exemplary embodiment, feature classification circuitry 14 is primarily comprised of transistors and a few resistors and capacitors. As described elsewhere herein, the sampled feature voltages, $V_{ZCR,SH}$ and $V_{ENERGY,SH}$, drive this module. Feature classification circuitry 14 operates in continuous time, but it is effectively discrete-time because $V_{ZCR,SH}$ and $V_{ENERGY,SH}$ are discrete-time voltages. Feature classification circuitry 14 essentially creates a threshold, where that threshold is an "effective" hyperplane line. The term "effective" is used because if you sweep the entire range of possible $V_{ZCR,SH}$ and $V_{ENERGY,SH}$ values that can be input to the hyperplane circuit, you will find that on one side of this "effective" line, the $V_{PATENCY}$ value is low and on the other side of the line the $V_{PATENCY}$ value is high. In the exemplary embodiment, feature classification circuitry 14 is similar to and may employ the classifier design 70 described in B. Gestner, et al, "Glass break detector analog front-end using novel classifier circuit," in 2007 *IEEE International Symposium on Circuits and Systems*, IEEE, 2007, pp. 3586-3589, which is shown in FIG. 6.

Figure 7:
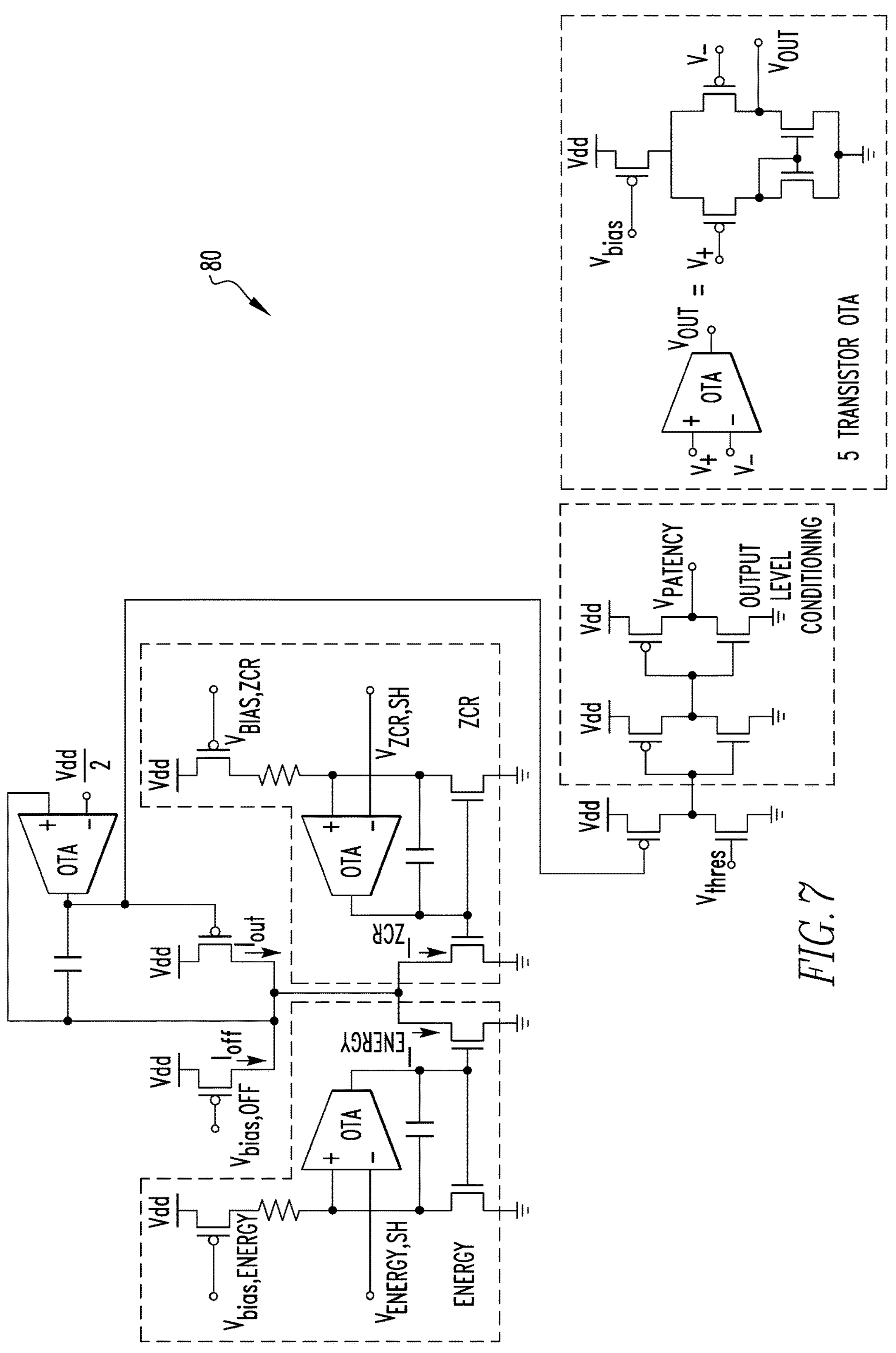
FIG. 7 is a schematic diagram of alternative classification circuitry that may be used as a part of the system of FIG. 1 according to another particular non-limiting exemplary embodiment of the disclosed concept.

In an alternative embodiment, feature classification circuitry 14 may employ classifier design 80 shown in FIG. 7. Classifier design 80 is similar to classifier design 70. Classifier design 80 uses two features (i.e., the "ENERGY" and "ZCR" blocks in the figure), as well as two series resistors shown in the "ENERGY" and "ZCR" blocks to improve control over shaping the discriminating hyperplane line. The $V_{ENERGY,SH}$ and $V_{ZCR,SH}$ are the sampled $V_{ENERGY}$ and $V_{ZCR}$ voltages, respectively, as described herein. $V_{bias,OFF}$ is the bias voltage that controls the $I_{off}$ current, which is described by Gestner et al. $V_{thres}$ is described by Gestner et al. and relates to control of the discriminating hyperplane line. $V_{bias,ENERGY}$ and $V_{bias,ZCR}$ control the current through the current mirror branches in the "ENERGY- and ZCR" blocks. $V_{PATENCY}$ is the circuit's binary output estimate of blood vessel patency. The PMOS devices are ALD1107 and ALD1117 matched transistor packages, and the NMOS devices are ALD1106 and ALD1116 matched transistor packages.

In one particular exemplary embodiment, a majority vote protocol is utilized and implemented in free flap patency monitoring system 2 in order to provide more accurate results. In particular, in such an implementation, multiple windowed classification decisions as described herein are acquired for a period of time, such as, without limitation, one second or thirty seconds, and then a majority vote is used to determine the $V_{PATENCY}$ value (high or low) for that period. The majority vote based $V_{PATENCY}$ value for each period is transmitted by free flap patency monitoring system 2 as described herein for use by an individual, such as a clinician or other operator. In the exemplary embodiment, free flap patency monitoring system 2 is provided with voting protocol circuitry that is structured to aggregate the $V_{PATENCY}$ decisions across the predetermined observation period (e.g., one or thirty seconds as noted above) and calculate and output the majority vote based $V_{PATENCY}$ value.

Thus, as described in detail herein in various particular embodiments, the disclosed concept provides a hardware-only free flap patency monitoring system that is capable of detecting flap failures before they happen, that provides a simple binary output indicator of free flap patency status, and that does not require any operator experience to interpret.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of monitoring patency of a free flap connected to a blood supply including a blood vessel, comprising:

in a plurality of hardware-only circuitry modules implemented as part of a monolithic microchip and coupled to a transmit transducer coupled to the blood vessel and a receive transducer coupled to the blood vessel:

insonifying a blood flow volume within the blood vessel through the transmit transducer;

receiving a scattered signal from the receive transducer, the scattered signal being generated in response to the blood flow volume being insonified;

extracting a baseband Doppler blood flow signal, $V_{BASEBAND}$, from the scattered signal;

extracting a plurality of features from $V_{BASEBAND}$, the plurality of features including a measure of a zero crossing rate of $V_{BASEBAND}$ and a measure of an energy of $V_{BASEBAND}$; and classifying the plurality of features and generating a binary signal based on the classification of the plurality of features, wherein the binary signal will have a first state responsive to the classification of the plurality of features indicating that a flow rate within the blood vessel is less than a predetermined level and a second state responsive to the classification of the plurality of features indicating the flow rate within the blood vessel is greater than or equal to the predetermined level;

wherein the plurality of hardware-only circuitry modules include:

analog front end circuitry coupled to the transmit transducer and the receive transducer, wherein the analog front end circuitry performs the insonifying of the blood flow volume through the transmit transducer, the receiving of the scattered signal from the receive transducer, and the extracting of $V_{BASEBAND}$;

zero crossing feature extractor circuitry coupled to the analog front end circuitry, wherein the zero crossing feature extractor circuitry receives $V_{BASEBAND}$ from the analog front end circuitry and generates, for a predetermined window period, a first voltage signal, $V_{ZCR}$, based on $V_{BASEBAND}$ that is a measure of a zero crossing rate of $V_{BASEBAND}$ and that comprises a first one of the plurality of features;

energy feature extractor circuitry coupled to the analog front end circuitry, wherein the energy feature extractor circuitry receives $V_{BASEBAND}$ from the analog front end circuitry and generates, for the predetermined window period, a second voltage signal, $V_{ENERGY}$, based on $V_{BASEBAND}$ that is a measure of an energy of $V_{BASEBAND}$ and that comprises a second one of the plurality of features;

signal sampling circuitry coupled to the zero crossing feature extractor circuitry and the energy feature extractor circuitry, wherein the signal sampling circuitry receives $V_{ZCR}$ and generates a first sampled signal, $V_{ZCR}$ SH, from $V_{ZCR}$ and receives $V_{ENERGY}$ and generates a second sampled signal, $V_{ENERGY}$, SH, from $V_{ENERGY}$; and feature classification circuitry coupled to the signal sampling circuitry, wherein the feature classification circuitry performs the classifying of the plurality of features and the generating of the binary signal based on at least $V_{ZCR,SH}$ and $V_{ENERGY,SH}$;

wherein the method further comprises implementing in the plurality of hardware-only circuitry modules a voting protocol to generate the binary signal based on $V_{ZCR,SH}$ and $V_{ENERGY,SH}$ and a number of additional sampled signals generated from $V_{BASEBAND}$ during a predetermined time period.

2. The method according to claim 1, wherein the classifying the plurality of features and generating the binary signal based on at least $V_{ZCR,SH}$ and $V_{ENERGY,SH}$ employs a two-dimensional dividing hyperplane where $V_{ZCR,SH}$ and $V_{ENERGY,SH}$ are classified as being on one side of the dividing hyperplane or the other.

3. The method according to claim 1, wherein the zero crossing feature extractor circuitry is structured to detect negative-going (i.e., high-to-low) zero-crossings.

4. The method according to claim 3, wherein the zero crossing feature extractor circuitry includes a comparator, a one-shot pulse generator which is falling-edge triggered, and a current source triggered by pulses from the one-shot pulse generator that drives a current onto a sampling capacitor for integration.

5. The method according to claim 1, wherein the energy feature extractor circuitry comprises a peak detector formed by two op-amps which perform level shifting, and a diode, a resistor, and a capacitor located between the op-amps.

* * * * *